[12] United States Patent  
Leroux et al.

(10) Patent No.: US 8,815,944 B2  
(45) Date of Patent: Aug. 26, 2014

(54) PHARMACEUTICAL COMPOSITION WITH GELLING PROPERTIES CONTAINING A TYROSINE DERIVATIVE

(75) Inventors: Jean-Chrisophe Leroux, Montreal (CA); Guillaume Bastiat, Montreal (CA)

(73) Assignees: Ethypharm, Saint-Cloud (FR); Universite de Montreal, Montreal Quebec (CA)

( * ) Notice: Subject to any disclaimer, the term of this patent is extended or adjusted under 35 U.S.C. 154(b) by 749 days.

(21) Appl. No.: 12/864,909

(22) PCT Filed: Jan. 30, 2009

(86) PCT No.: PCT/EP2009/051085  
§ 371 (c)(1),  
(2), (4) Date: Nov. 11, 2010

(87) PCT Pub. No.: WO2009/095485  
PCT Pub. Date: Aug. 6, 2009

(65) Prior Publication Data  
US 2011/0207813 A1 Aug. 25, 2011

Related U.S. Application Data

(60) Provisional application No. 61/025,107, filed on Jan. 31, 2008.

(30) Foreign Application Priority Data

Jan. 31, 2008 (FR) ...................................... 08 50617

(51) Int. Cl.  
*A61K 31/27* (2006.01)  
*A61K 47/16* (2006.01)  
*A61P 25/28* (2006.01)  
*A61K 47/18* (2006.01)  
*A61K 47/32* (2006.01)  
*A61K 47/44* (2006.01)  
*A61K 9/00* (2006.01)

(52) U.S. Cl.  
CPC .............. *A61K 31/27* (2013.01); *A61K 47/183* (2013.01); *A61K 47/32* (2013.01); *A61K 47/44* (2013.01); *A61K 9/0024* (2013.01)  
USPC .......................................... 514/490; 514/785

(58) Field of Classification Search  
CPC ..... A61K 31/27; A61K 47/183; A61K 47/32; A61K 47/44; A61K 9/0024  
See application file for complete search history.

(56) References Cited

U.S. PATENT DOCUMENTS 3,969,087 A 7/1976 Saito et al.  
6,464,987 B1 10/2002 Fanara et al.  
7,691,408 B2 4/2010 Leroux et al.  
2005/0031650 A1 2/2005 Leroux et al.  
2006/0121115 A1* 6/2006 Leroux et al. ................. 424/486

FOREIGN PATENT DOCUMENTS

FR 2281162 3/1976  
WO WO 99/56725 11/1999  
WO WO 03/075885 A1 9/2003  
WO WO 2006/037113 A2 4/2006

OTHER PUBLICATIONS

Heinrich Huhnerfuss, Role of Hydrogen Bond and Metal Complex Formation for Chiral discrimination in Amino Acid Monolayers studied by infrared reflection-Absorption Spectroscopy, 1996, Langmuir, 12, 2561-2569.*  
Heinrich Huhnerfuss, The determination of the molecular order of chiral monolayers at athe air-water interface by infrared reflection-absorption spectroscopy—a bridge between physico-and biochemistry, 1996, Thin Solid Films, 694-697.*  
I. Gulcin, Comparison of in vitro antioxidant and antiradical activities of L-tyrosine and L-Dopa, 2006, Amino Acids, 32:pp. 431-438.*  
Sudipta Ray, Smart oligopeptide gels: in situ formation and stabilization of gold and silver nanoparticles within supramolecular organogel networks, 2006, Chem. Comm., 2816-2818.*  
Sudaxshina Mudan, Organogels in drug delivery, 2005, Expert Opin. Drug Deliv., 2(3) pp. 1-17.*  
Sudipta Ray, Smart oligopeptide gels: in situ formation and stabilization of gold and silver nanoparticles within supramolecular organogel network, Chem. Commun., 2006, pp. 2816-2818.*  
Keith J. Stine, Fluorescence microscopy study of langmuir monolayers of racemic and enantiomeric N-stearoyltyrosine, Chemistry and Physics of Lipids, 69, 1994, pp. 41-50.*

(Continued)

*Primary Examiner* — Julie Ha  
*Assistant Examiner* — Erinne Dabkowski  
(74) *Attorney, Agent, or Firm* — Ratnerprestia

(57) ABSTRACT

The present invention relates to an injectable pharmaceutical composition with gelling properties containing: -an active principle; a hydrophobic and bio-compatible organic liquid; and an organogelling substance, the molecules of which have the capacity to bind together via bonds of low energy, wherein the organogelling substance is chosen among L-tyrosine derivatives responding to the following formula (I) wherein: R1 is an alkyl group containing 1 to 3 carbon atoms, linear or branched; and R2 is a hydrophobic group chosen among aliphatic saturated or unsaturated fatty chains or aryl or arylalkyl groups. Its use as a vector for the release of active principles, as well as its process of preparation.

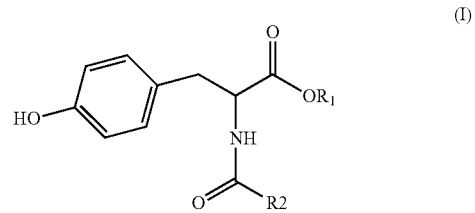

(I)

31 Claims, 4 Drawing Sheets

(56) References Cited

OTHER PUBLICATIONS

Lim et al., "Limonene GP1/PG Organogel as a Vehicle in Transdermal Delivery of Transdermal Delivery of Haloperidol" International Journal of Pharmaceutics, 2006, vol. 311, pp. 157-164.

Luo et al., "Self-Assembled Organogels Formed by Mono-Chain L-Alanine Derivatives" Chem. Commun., 2001, No. 17, pp. 1556-1557.

Upadhyay et al., "Sorbitan Ester Organogels for Transdermal Delivery of Sumatriptan" Drug Development and Industrial Pharmacy, 2007, vol. 33, pp. 617-625.

Vintiloiu et al., "Organogels and their use in Drug Delivery—A review" Journal of Controlled Release, 2008, vol. 125, No. 3, pp. 179-192.

Ray, Sudipta; Das, Apurba Kumar; and Banerjee, Arindam;"Smart Oligopeptide Gels" in Situ Formation and Stabilization of Gold and Silver Nanoparticles Within Supramolecular Organogel Networks'—Supplemental Materials; The Royal Society of Chemistry 2006, pp. S1-S26.

\* cited by examiner (a) B-TyrOCH₃

(b) S-TyrOCH₃

(c) L-TyrOCH₃

PHARMACEUTICAL COMPOSITION WITH GELLING PROPERTIES CONTAINING A TYROSINE DERIVATIVE

CROSS REFERENCE TO RELATED APPLICATIONS

This application is the U.S. National Phase application of PCT International Application No. PCT/EP2009/051085, filed Jan. 30, 2009, which claims priority of U.S. Patent Provisional Application No. 61/025,107, filed Jan. 31, 2008, and also claims priority of French Patent Application No. 0850617, filed Jan. 31, 2008, the disclosures of which are incorporated herein by reference in their entireties for all purposes.

FIELD OF THE INVENTION

The present invention relates to a pharmaceutical composition with gelling properties comprising a hydrophobic organic liquid, an organogelling substance comprising a derivative of L-tyrosine, and an active principle. Said pharmaceutical composition may be injected to a living organism and forms a gel usable as vector for the sustained delivery of said active principle. The present invention further relates to a process for preparing said pharmaceutical composition.

BACKGROUND OF THE INVENTION

Gels correspond to an intermediate state of matter containing both solid and liquid components. The solid elements form a three-dimensional structure or matrix, organized as a network of mutually interconnected molecules. This network immobilizes the elements present in liquid form.

In hydrogels, the liquid medium is aqueous, whereas in organogels the liquid medium is an organic solvent.

Gels may also be classified based on the nature of the bonds that link together the molecules of the solid elements. Chemical gels arise when strong covalent bonds hold the network together, and physical gels when hydrogen or Van der Waals bonds or electrostatic interactions maintain the gel network.

In the case of heat-sensitive gels, the temperature at which the change of state is observed is known as the transition temperature. In the particular case of systems showing hysteretic behaviour, the gel/liquid transition temperature is different from the liquid/gel transition temperature.

Gels may be used in the pharmaceutical industry for their retention capacity with respect to bioactive molecules, especially in the context of a transcutaneous administration of active substances. Also, implantable gels have already been used for in situ delivery of active principle. However, this type of use necessitates the surgical implantation of a preformed gel, operation that remains both expensive and a limitation for the patient.

Organogels are systems composed of an organic solvent with a three-dimensional network of self-assembled compounds. The compounds, commonly called "organogelators" or "organogelling substances", are essentially low molecular weight molecules. The physical association between organogelator molecules forms a solid network which is able to immobilize the organic solvent. Research on these matrices is recent and has grown rapidly with the continuous development of organogelator molecules.

Unfortunately, there are only few studies describing the use of organogels in drug delivery. This can be partly explained by the fact that most matrices under investigation may be potentially toxic. In the pharmaceutical field, organogels have been mainly studied for the transdermal delivery of drugs (Upadhyay K K et al, 2007 and Lim P F C et al., 2006).

WO99/56725 describes a composition containing phospholipids as organogelators, dedicated to be injected into a body, and that forms spontaneously a gel when encountering physiological fluids. Such a composition can be easily used as a vector for active principle. Before injection, it is liquid. After injection, it gels by absorbing the surrounding aqueous phase.

Other work also reports organogels that can be injected and serve as active principle carriers, based on alanine methyl ester, that are modified with a stearoyl chain ($C_{18}$): $S$-AlaOCH$_3$ (WO03/075885). This type of organogelator has the advantages of a straightforward synthesis and bio compatibility. This organogel serves as a support for the sustained release of active principles by diffusion and/or erosion and/or gradual biodegradation of the organogel in the body. In this case, organogels are formed by diffusion of an hydrophilic solvent added to the composition, or by cooling of the site of injection during several minutes.

The present invention is based on the surprising discovery by the present inventors that Tyrosine derivatives such as N-Behenoyl L-tyrosine methyl ester (B-TyrOCH$_3$) or N-Stearoyl L-tyrosine methyl ester (S-TyrOCH$_3$) are able to form organogels with improved physical properties, for example a better gel hardness, especially compared to those obtained from alanine derivatives. This property may allow to decrease the concentration of organogelator in the organogel, and hence to increase the concentration of active principle in the organogel. It may also permit to obtain implants that resist in vivo longer than Alanine-based organogels, hence releasing the drug for a longer time than the S-AlaOCH$_3$ formulations.

The organogel according to the present invention, when obtained with a low concentration of organogelling substance, is already in gel state before injection. Contrary to compositions of the prior art, there is no need of cooling, diffusing nor absorbing fluids to form the gel in situ in a body.

In addition, the composition according to the present invention has the advantage of being extremely inexpensive, both in terms of manufacture as is described later, and in terms of packaging and administration.

DETAILED DESCRIPTION OF THE INVENTION

The first object of the present invention is to provide an injectable pharmaceutical composition with gelling properties containing an active principle, a hydrophobic and biocompatible organic liquid, and an organogelling substance, the molecules of which have the capacity to bind together via bonds of low energy, wherein said organogelling substance is chosen among L-tyrosine derivatives responding to the following formula (I):

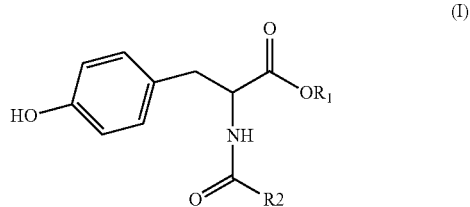

wherein:
R1 is an alkyl group containing 1 to 3 carbon atoms, linear or branched; and
R2 is a hydrophobic group chosen among aliphatic saturated or unsaturated fatty chains or aryl or arylalkyl groups.

[Organogeltor]

As explained above, organogels are systems composed of an organic liquid solvent embedded within a three-dimensional solid network of self-assembled compounds. The compounds, commonly called "organogelators" or "organogelling substances", are essentially low molecular weight molecules. According to the present invention, the compound is characterized in that it is a derivative of the amino acid L-tyrosine responding to the formula (I) as defined above.

R1 is an alkyl group containing 1 to 3 carbon atoms, linear or branched. R1 can be a methyl (—$CH_3$), an ethyl (—$C_2H_5$), a isopropyl (—$C_3H_7$) or an n-propyl (—$C_3H_7$) group. More preferably, R1 is a methyl (—$CH_3$).

R2 is a hydrophobic group chosen to confer sufficient hydrophobicity to the molecules of formula (I), thereby favouring the stability of the gel in the body. R2 is preferably chosen among aliphatic saturated or unsaturated fatty chains or aryl or arylalkyl groups. According to the present invention, an aliphatic fatty chain is an open hydrocarbonated chain, linear or branched, derived from a fatty acid. The natural fatty acids contain between 4 and 28 carbon atoms. The higher the number of carbons forming the chain is, the more hydrophobic is the fatty chain.

Aliphatic fatty chains comprise saturated chains (with no double bond) and unsaturated chains (with at least one double bond). Unsaturated chains may be monounsaturated (only one double bond) or poly-unsaturated (several double bonds).

Preferably, R2 is a fatty chain comprising between 11 and 24 carbon atoms, preferably between 17 and 21, most preferably comprising 17 or 21 carbon atoms.

Alternatively, R2 may be an aryl group i.e. a system comprising one or more aromatic carbonated ring comprising 5 or 6 carbon atoms, e.g. a phenyl, bi-phenyl, or naphtyl.

Alternatively, R2 may be an arylalkyl group, i.e. an aryl group linked to the rest of the molecules with a $C_1$-$C_6$ alkyl group, e.g. benzyl or phenyl ethyl.

Even more preferably, R2 responds to the formula —$(CH_2)_n$—$CH_3$, where n is an integer comprised between 10 and 23, preferably is between 16 and 20, most preferably is 16 or 20.

Preferably, the organogelling substance is chosen among N-Behenoyl L-tyrosine methyl ester (B-TyrOCH$_3$) (FIG. 1a), N-Stearoyl L-tyrosine methyl ester (S-TyrOCH$_3$) (FIG. 1b) and N-Lauroyl L-tyrosine methyl ester (L-TyrOCH$_3$) (FIG. 1c).

The molecules of the organogelling substance according to the present invention are capable of binding together via bonds of low energy, for example Van der Waals forces or hydrogen bonds. It is believed that two hydrogen-bonds from the NH and OH functions of the molecules of formula (I) are implicated in the organogelator network. By contrast, only one hydrogen-bond is involved in the alanine-based system of the prior art, which may explain the improved gelling properties of the Tyrosine-based system of the present invention.

As the organogelling substance according to the present invention is a better organogelator than the alanine-based system of the prior art, the man skilled in the art can use a lower concentration of organogelator in the composition. Hence, the concentration of organogelator represents between 0.5% and 10% by weight relative to the total weight of the composition according to the present invention, but is preferably between 1% and 5%, and most preferably between 1% and 3%.

Moreover, the organogelling substance according to the present invention is preferentially bio-compatible and does not give rise to toxic amounts of metabolites during its degradation by the body.

[Hydrophobic and Bio-Compatible Organic Liquid]

The composition according to the present invention contains a hydrophobic and bio-compatible organic liquid. The expression "hydrophobic organic liquid" means an organic solvent or mixture of organic solvents whose molecules or parts of molecules have a high level of repulsion towards water molecules. The hydrophobic organic liquid is essentially water-immiscible. It is bio-compatible, i.e. tolerated by the host organism, and trigger little or no immune reaction, for example of inflammatory or allergic type.

Organic solvents that can be bio-degraded slowly, i.e. not rapidly metabolized by the enzymes present at the site of injection, and especially by lipases, will preferably be used.

It is preferable to use hydrophobic organic solvents that are liquid at room temperature (between 18 and 25° C.), which simplifies the process for manufacturing and administering the composition in accordance with the invention.

The hydrophobic organic liquid according to the present invention can be chosen among vegetable oils, synthetic or semi-synthetic oils, and their mixtures. The mixtures of different hydrophobic organic solvents may present the advantage of modifying the gelation profile of the composition or of facilitating the dissolution of certain active principle into the composition.

Among the synthetic or semi-synthetic solvents that may be used as the hydrophobic organic liquid in accordance with the present invention, mention may be made especially of silicone oil, squalene, benzyl benzoate, benzyl chloride and benzyl benzoate/benzyl alcohol mixtures or Crodamol® GTCC-PN, as well as their mixtures. According to the present invention, the vegetable oil can be chosen among safflower oil, soybean oil, olive oil, castor oil, corn oil, sesame oil or almond oil and their mixtures.

The hydrophobic organic liquid in accordance with the invention preferably contains mono-, di- and/or tri-glycerides. Hydrocarbonated chains of said triglycerides may comprise between 11 and 24 carbon atoms, preferably between 17 and 21 carbon atoms. Safflower oil, which presents suitable gelling behaviour, slow biodegradability and excellent bio-compatibility, will preferably be used as the hydrophobic organic liquid.

[Active Principle]

The composition according to the present invention at least one active principle. The expression "active principle" means any substance that has the capacity to act on a living organism (bio-active) or its functioning so as to prevent, cure, relieve or improve the condition of the said organism.

The active principles that may be released into the body from the organogel in accordance with the present invention are advantageously substances that are difficult to package for a sustained release, such as low molecular weight molecules of hydrophilic or very hydrophilic nature.

The active principle can be incorporated into the composition according to the present invention by dispersion or dissolution. It can be hydrophilic or hydrophobic or amphiphilic.

The composition according to claim 11, wherein the active principle is chosen among drugs, such as morphine, heparin, anticholinesterase such as rivastigmine, galantamine, donepezil, or N-methyl-D-aspartate receptor antagonists such as memantine, proteins, such as α or β interferon, antibodies or interleukins, hormones, such as human growth hormone, somatostatin, erythropoietin thyreotrope hormone or leuprolide, peptides, amino acids, vitamins, nucleic acids, nucleic acid derivatives and oligonucleotides.

These examples are in no way limiting, and other types of molecules, in particular other proteins, may be entirely envisaged for such a sustained release from an organogel in accordance with the invention. The present invention may thus be used for a large number of substances of therapeutic or medical interest for which a sustained release into the body is desired.

Advantageously, the said active principle will be used in proportions from 0.5% to 5% by weight of the composition according to the invention.

[Hydrophilic Organic Solvent]

The composition according to the present invention may further comprise an hydrophilic organic solvent which helps to liquefy the composition. In that case, the composition according to the present invention becomes softer or liquid, and its gelation or hardening is induced by diffusion of said hydrophilic organic solvent into the physiological liquids in vivo. According to the invention, the expression "hydrophilic organic solvent" means a solvent that has high affinity for aqueous media, i.e. that is water-miscible.

The hydrophilic organic solvent, when introduced into the composition according to the invention, comes into competition with the molecules of organogelling substance, creating with said molecules weak bonds (e.g. hydrogen bridges) that prevent the said molecules from self-assembling into a dense and unified network. The composition according to the invention thus remains in liquid form or semi-solid state for as long as the molecules of the said hydrophilic organic solvent remain bound to the organogelling molecules. After being injected into an animal body, especially human, the composition is in contact with physiological fluids. The diffusion of the said hydrophilic organic solvent in the physiological fluids allows the molecules of said organogelling substance to self-assemble or complete the self-assembling process. By creating a structured network, this self-assembly allows the hydrophobic organic liquid to be retained, causing the said composition to change from the liquid or semi-solid state to the gelled state.

The hydrophilic organic solvent according to the present invention can be chosen among ethanol, glycerol, benzyl alcohol, propylene glycol, N-methylpyrrolidone (NMP) and dimethyl sulfoxide (DMSO), poly(ethylene)glycol of low molecular weight, chlorobutanol, furfural, N,N-dimethyl-acetamide, glycerol formal, isopropylidene-glycerol, ethyl lactate, acetic acid and lactic acid. These examples are not limiting, and it may be entirely envisaged to perform the invention using other hydrophilic organic solvents with gel-destabilizing properties, i.e. the capacity to create weak bonds with the organogelling substance in accordance with the invention.

The amount of said hydrophilic solvent in the composition is preferably less than 60%, more preferably less than 20%, even more preferably less than 10% by weight of the composition.

[Physical Properties of the Composition]

The pharmaceutical injectable composition according to the present invention do form a implant after injection to a body, allowing the release of active substances in said body over long periods of time.

The term "injectable" means that the composition can be injected with a needle (18 or 20 G)

When extemporaneously prepared, the composition according to the invention is in soft gel state which is compatible with injection. If necessary, a hydrophilic organic solvent may be added to the composition to facilitate the injection as previously explained. After the injection in vivo, the organogel remains stable at the temperature of the body.

Preferably, the composition according to the present invention is in a soft gel state at the room temperature (25° C.). The composition according to the present invention is heat-sensitive, and preferably has a transition temperature from the gel state to the liquid state above 37° C., more preferably above 45° C.

Moreover, the present invention has hysteretic properties. The term "hysteresis" means the physical phenomenon observed especially for gelable compositions, representing the difference existing between the gel/liquid transition temperature and the liquid/gel transition temperature.

The composition according to the present invention can be further characterized in term of hardness by differential scanning calorimetry (DSC) to obtain gel-liquid or gel-solution transition temperatures ($T_{GS}$) and enthalpy values of the transition ($\Delta H$). Also, rheological analysis of the gels can be performed to determine the gel hardness, by measuring the complex modulus G* (see example 5). G* characterizes the overall resistance to deformation of a material, regardless of whether that deformation is recoverable (elastic) or non-recoverable (viscous).

The composition according to the present invention has preferably a complex modulus G* above 15 kPa and/or a transition enthalpy above 40 kJ/mol.

[Use as a Delivery System]

A further object of the present invention is the pharmaceutical composition as previously defined, for its use as a medicament.

By delivering a therapeutic substance during several days in an organism, the composition according to the invention may be used as a medicament especially as a vector for sustained release of active principles into the body.

Said vector is able to release the said active principles into the body over a period of time of at least 50 hours, preferably at least 100 hours, and even at least 150 hours.

Active substances embedded within the composition, especially hydrophilic substances, can be retained inside the organogel as long as the organogel is present inside the body. Said organogel has the capacity to be eliminated slowly by gradual erosion and/or biodegradation, without toxicity to the body in which it is implanted, thus releasing the active substance. The advantage of using such a hydrophobic organogel to deliver a hydrophilic therapeutical substance is to avoid its initial burst of release and secondary effects due to the rapid diffusion of said substance toward physiological fluids. The bio-active principle will diffuse into the body from the organogel continuously.

The organogel formed from the composition according to the invention is able to retain bioactive molecules and more particularly molecules less than 100 000 daltons in weight, of hydrophilic or hydrophobic nature.

The composition according to the present invention may be administered using a conventional syringe with needle 20 G, and injected into the body via the parenteral route, especially subcutaneously, intradermally, intraperitoneally, intramuscularly, intraocularly or vaginally, to an open wound or during surgery. The expression "parenteral route" means any route of penetration into the body other than the digestive route. Vascular route injection may be envisaged if very small organogels are generated.

The invention further covers the process for preparing the composition previously described, comprising the three following steps:
- (a) Mixing the active principle, the organogelling substance and the hydrophobic organic liquid all together,
- (b) Heating the mixture obtained in step (a) at a temperature higher than the transition temperature from the gel state to the liquid state of said composition, until complete dissolution of the organogelling substance,
- (c) Cooling the mixture obtained in step (b) at room temperature.

Alternatively, a hydrophilic organic solvent as previously described may also be added to the mixture obtained at step (b), just before cooling.

Such composition are injectable and form in vivo an implant that releases continuously the embedded active principle (see example 6).

FIGURES

Figure 1:
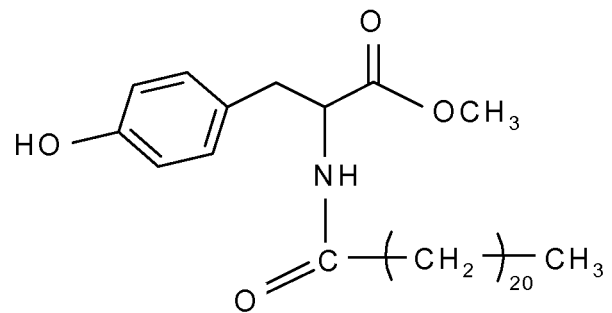
FIG. 1 shows the structural formula of three organogelators according to the present invention: (a) N-Behenoyl L-tyrosine methyl ester (B-TyrOCH3), (b) N-Stearoyl L-tyrosine methyl ester (S-TyrOCH3) and (c) N-Lauroyl L-tyrosine methyl ester (L-TyrOCH3).
Figure 1:
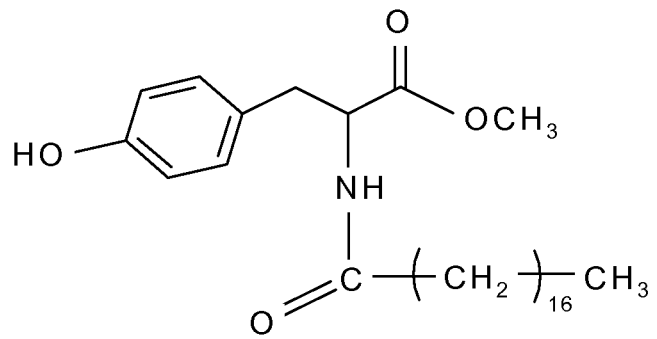
Figure 1:
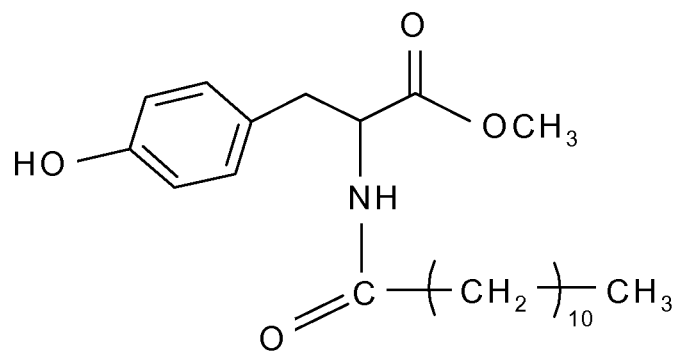

The graph shows the plasma concentration of rivastigmine after the subcutaneous administration of a 5 mg/kg dose of rivastigmine hydrogen tartrate dispersed in oil (■) (oil formulation), and 15 mg/kg doses of rivastigmine hydrogen tartrate dispersed in 5% (w/w) B-TyrCH$_3$ gel (□) (gel formulation). (Mean±SD, n=8).

EXAMPLES

Example 1

Synthesis of Organogelators According to the Present Invention

N-Stearoyl L-Tyrosine Methyl Ester (S-TyrOCH$_3$) is prepared by reaction of L-Tyrosine methyl ester hydrochloride (HCl-TyrOCH$_3$) with N-Stearoyl chloride (S—COCl), as described thereafter.

HCl-TyrOCH$_3$ (1.5 g, 1.1 eq) is suspended in 50 mL of chloroform in an ice bath. Triethylamine (1.80 mL, 2.2 eq) is added dropwise to the cold solution. The solution becomes limpid. After 15 min under stirring, S—COCl (1.78 g, 1 mol eq) is slowly added (dropwise) to the cold reaction mixture, in order to control the exothermic reaction. After 2 hours at 0° C., the mixture is heated at 45° C. overnight. The mixture remains clear.

The mixture is successively washed with water, a saturated aqueous solution of NaHCO$_3$, brine, a solution of KHSO$_4$ (1M), a solution of HCl (5-10%) and again water. The organic phase is dried (MgSO$_4$), filtered, and concentrated under vacuum. The resulting colorless powder is purified by crystallization from ethyl acetate/cold hexane (ratio 4/1 v/v) and a white powder of S-TyrOCH$_3$ is obtained.

Reaction:

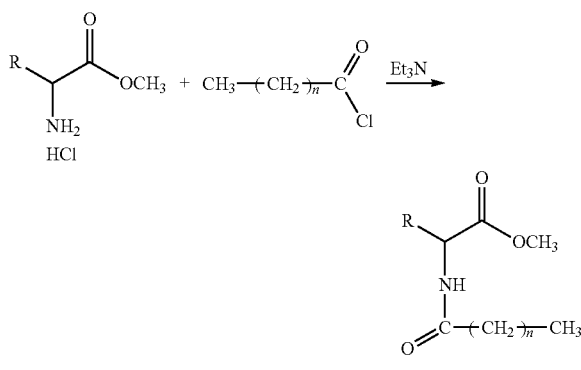

N-behenoyl L-tyrosine methyl ester (B-TyrOCH$_3$) is prepared the same way by reaction of L-Tyrosine methyl ester and N-Behenoyl chloride (B—COCl). N-lauroyl L-tyrosine methyl ester (L-TyrOCH$_3$) is prepared the same way by reaction of L-Tyrosine methyl ester and N-lauroyl chloride (L-COCl).

Example 2

Characterization of the Organogelators Prepared at Example 1

1/N-Stearoyl L-Tyrosine Methyl Ester (S-TyrOCH$_3$)

Molecular formula: $C_{28}H_{47}O_4N$.

Mass spectroscopy: Theoretical molecular weight: 461.68 g·mol$^{-1}$. Experimental molecular weight: 461.2 g·mol$^{-1}$ $^1$H-NMR (400 MHz, CDCl$_3$) δ (ppm): 0.88 (t, 3H), 1.25 (m, 28H), 1.6 (m, 2H), 2.17 (t, 2H), 3.05 (d-quad, 2H), 3.74 (s, 3H), 4.88 (quad, 1H), 5.89 (d, 1H) et 6.7-7.0 (m, 4H).

Elemental analysis: Theoretical: C 72.84%; H 10.26%; N 3.03%. Experimental: C 72.86%; H 11.25%; N 3.06%.

Yield: 77%.

Melting point: 103.7° C.

2/N-Behenoyl L-Tyrosine Methyl Ester (B-TyrOCH$_3$)

Molecular formula: $C_{32}H_{55}O_4N$.

Mass spectroscopy: Theoretical molecular weight: 517.78 g·mol$^{-1}$.

$^1$H-NMR (400 MHz, CDCl$_3$) δ (ppm): 0.88 (t, 3H), 1.25 (m, 36H), 1.57 (quint, 2H), 2.17 (t, 2H), 3.05 (d-quad, 2H), 3.73 (s, 3H), 4.87 (quad, 1H), 5.85 (d, 1H), 6.7-7.0 (m, 4H).

Elemental analysis: Theoretical: C 74.23%; H 10.71%; N 2.71%. Experimental: C 74.06%; H 11.50%; N 2.86%.

Yield: 80%.

3/N-Lauroyl L-Tyrosine Methyl Ester (L-TyrOCH$_3$)

Molecular formula: $C_{22}H_{35}O_4N$.

Mass spectroscopy: Theoretical molecular weight: 377.52 g·mol$^{-1}$. Experimental molecular weight: 377.1 g·mol$^{-1}$.

$^1$H-NMR (400 MHz, CDCl$_3$) δ (ppm): 0.88 (t, 3H), 1.25 (m, 28H), 1.58 (quint, 2H), 2.18 (t, 2H), 3.04 (d-quad, 2H), 3.74 (m, 3H), 4.89 (m, 1H), 5.94 (d, 1H), 6.7-6.95 (m, 4H).

Elemental analysis: Theoretical: C 69.99%; H 9.34%; N 3.71%. Experimental: C 68.31%; H 9.30%; N 3.92%.

Yield: 41%.

Melting point: 86.7° C.

Example 3

Formation of Tyrosine-Based Organogel

Safflower oil is used as hydrophobic organic solvent in accordance with the invention. The organogelling substance chosen is N-stearoyl L-tyrosine methyl ester (S-TyrOCH$_3$).

The following table summarizes the used proportions.

| Product | Function | Proportion |
|---------|----------|------------|
| S-TyrOCH$_3$ | Organogelator | 5% w/w |
| Safflower oil | Hydrophobic organic solvent | Qs ad 5 mL |

Organogelator and safflower oil in adequate proportion were mixed and heated at a temperature higher than $T_{GS}$, until dissolution of the organogelator. The solution was cooled at room temperature and the gel was obtained.

Example 4

In Vivo Injection of Tyrosine-Based Organogel

Safflower oil is used as hydrophobic organic solvent in accordance with the invention. The organogelling substance chosen is N-behenoyl L-tyrosine methyl ester (B-TyrOCH$_3$). Proportions of the Composition:

| Product | Function | Proportion |
|---------|----------|------------|
| B-TyrOCH$_3$ | Organogelator | 5% w/w |
| Safflower oil | Hydrophobic organic solvent | Qs ad 5 mL |

The obtained composition is then injected subcutaneously in rats. The injection is performed in the dorsal area, using a conventional syringe (20 G needle) for subcutaneous injection. After 2 hours, the animal is sacrificed and a gel is extracted from the site of injection, demonstrating the presence of the organogel in vivo.

Example 5

Thermodynamic Characteristics of the Composition

Organogelators at a concentration of 5% (w/w) were solubilized in safflower oil at high temperature (>80° C.) and gels were obtained by cooling the mixture.

The gels were characterized by differential scanning calorimetry (DSC) to obtain gel-solution transition temperatures ($T_{GS}$) and enthalpy values of the transition (ΔH). Briefly, thermograms of gels were collected on a 2910 TA Instruments DSC system (New Castle, Del.). The instrument was calibrated with indium. Gels were weighed into aluminum pans that were subsequently sealed. Temperature was scanned between 5 and 90° C. at 10° C./min. The reported gel-sol transition temperatures ($T_{GS}$) and enthalpies (ΔH) corresponded to the maximum and the area of the endothermic peaks respectively.

Rheological analysis of the gels was performed to determine the gel hardness, by measuring the complex modulus G*. The rheological properties of the organogels were measured by an AR2000 (Advanced Rheometer 2000, TA Instruments, New Castle, Del.), with parallel plate geometry (diameter of 40 mm). Organogels were heated until reaching $T_{GS}$ and they were placed between the parallel plates. The final thickness of the material coat between the plates was 650 to 750 μm. The film was cooled at 4° C. to form the gel. In the linear regime of the gel, the complex modulus G* have been measured as a function of the angular frequency (0.1 to 10 Hz) at 25±0.1° C. $G^* = (G'^2 + G''^2)^{0.5}$ with G' the storage modulus and G" the loss modulus.

TABLE 1

| # | $T_{GS}$ (° C.) | H (kJ · mol$^{-1}$) | G* (kPa) |
|---|---|---|---|
| S-Ala-OCH$_3$ | 60 | 55 | 5 |
| S-Trp-OCH$_3$ | 56 | 23 | <0.1 |
| S-Phe-OCH$_3$ | 43 | 38 | 6.1 |
| S-Tyr-OCH$_3$ | 65 | 50 | 15.2 |
| B-Phe-OCH$_3$ | 53 | 61 | 6 |
| B-Tyr-OCH$_3$ | 74 | 71 | 37.6 |
| S-Trp-OH | 122 | 16 | <0.1 |
| S-Tyr-OH | 127 | 18 | 5 |

Table 1 compares $T_{GS}$, ΔH, and G* for gels obtained from different organogelators. S-Ala-OCH$_3$ is described in WO03/075885. STrpOCH$_3$ means N-stearoyl L-tryptophan methyl ester; SPheOCH$_3$ means N-stearoyl L-phenylalanine methyl ester; S-TrpOH means N-stearoyl L-tryptophan; STyrOH means N-stearoyl L-tyrosine. Given their high $T_{GS}$, ΔH, and G* values, the Tyr-based organogelators appears to be the most resistant and hence most appropriate for the preparation of subcutaneous implant formulation. Moreover, the gels based on Tyrosine derivatives remain unaltered for several weeks when they are mixed with an aqueous buffer and mildly stirred.

Figure 2:
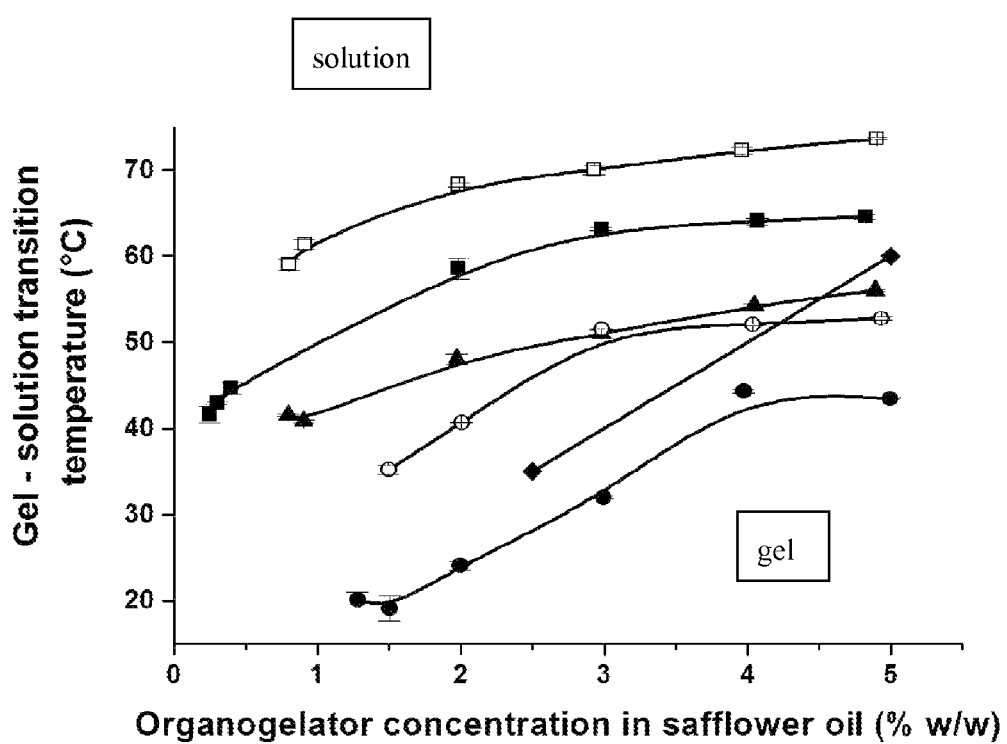
FIG. 2 shows the gel-solution ($T_{GS}$) transition temperature (in ° C.) of gels in safflower oil prepared from different organogelators and different concentrations of organogelators. (♦) S-AlaOCH$_3$ (6) (■) S-TyrOCH$_3$, (●) S-PheOCH$_3$, (▲) S-TrpOCH$_3$, (□) B-TyrOCH$_3$ and (○) B-PheOCH$_3$ (Ala is alanine, Tyr is tyrosine, Tip is tryptophan and Phe is phenylalanine)

FIG. 2 shows the thermograms of gels in safflower oil. Gels prepared with S-TyrOCH$_3$ and B-TyrOCH$_3$ display high $T_{GS}$. Even at concentrations as low as 1% (w/w), their $T_{GS}$ is above the physiological temperature (37° C.). The other derivatives exhibit lower $T_{GS}$, but all formulations are able to form gels at 37° C. when the organogelator concentration is above 4% (w/w).

Figure 3:
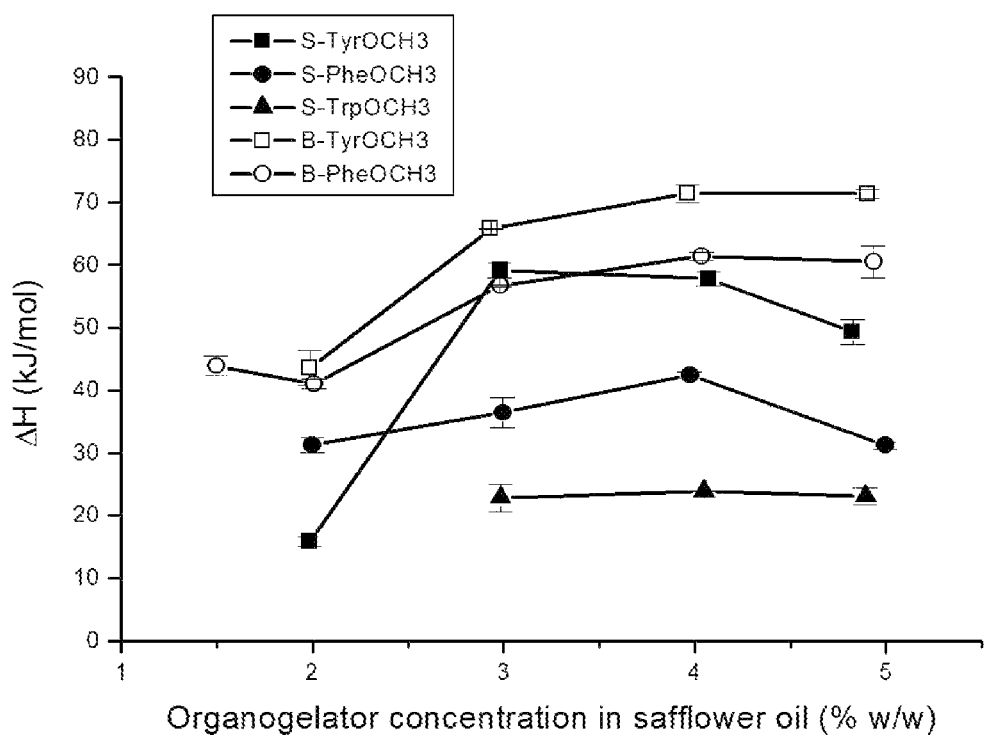
FIG. 3 shows the enthalpy variation (in kJ/mol) of gels in safflower oil prepared from different organogelators and different concentrations of organogelators. (■) S-TyrOCH$_3$, (●) S-PheOCH$_3$, (▲) S-TrpOCH$_3$, (□) B-TyrOCH$_3$ and (○) B-PheOCH$_3$. The variation of the enthalpy is measured by differential scanning calorimetry (DSC).

FIG. 3 shows enthalpy variation of gels in safflower oil.

Example 6

Pharmacokinetic of In Vivo Release of an Active Principle (Rivastigmine) from the Organogel All experimental procedures involving animals were conducted following a protocol approved by the Animal Care Committee of the University of Montreal in accordance with Canadian Council on Animal; Care guidelines. Male Long Evans rats (300-325 g) (Charles River Inc. St-Constant, QC, Canada) were housed for 1 week under controlled conditions (12-h light/dark schedule, 24° C.) prior to the start of experiments. Rat chow and tap water were provided ad libitum.

All formulation components were sterilized individually. B-TyrOCH$_3$ and rivastigmine hydrogen tartrate (Riv) were sterilized on dry ice by γ-radiation at 25 kGy using a $^{60}$Co source (Nordion Inc., Laval, QC, Canada). Stability of the organogelator and drug after sterilization was confirmed by $^1$H-NMR. The safflower oil and NMP were filtered on 0.2-μm polytetrafluoroethylene filters. Safflower oil, B-TyrOCH$_3$ (5% w/w) and Rivastigmine were mixed at 85° C. until solubilisation of the organogelator. N-methylpyrrolidone (NMP) (3% w/w) was added at high temperature, mixed and gel formulation syringes (20 G needle) were prepared, under aseptic conditions and put on ice during 15 minutes and at room temperature before injection. A control formulation was prepared without the organogelator in the same condition (oil formulation).

Composition of the Gel Formulation:

| Product | Function | Proportion |
| --- | --- | --- |
| Rivastigmine | Active principle | 1.5% w/w |
| B-TyrOCH$_3$ | Organogelator | 5% w/w |
| NMP | Hydrophilic organic solvent | 3% w/w |
| Safflower oil | Hydrophobic organic solvent | Qs ad 300 μL |

Composition of the Oil Formulation:

| Product | Function | Proportion |
| --- | --- | --- |
| Rivastigmine | Active principle | 0.5% w/w |
| NMP | Hydrophilic organic solvent | 3% w/w |
| Safflower oil | Hydrophobic organic solvent | Qs ad 300 μL |

The rats were divided into two groups (n=8) and given a single s.c. injection of approximately 300 μL of the appropriate formulation in the higher dorsal area using a 20-G syringe. Rats were injected with the following approximate rivastigmine doses: 5 mg/kg for oil formulation and 15 mg/kg for gel formulation. The exact amount of injected formulation was obtained by weight difference of syringes before and after injection.

Blood samples (400 μL) were periodically collected from the subclavian vein under isoflurane anaesthesia, and were subsequently centrifuged to collect plasma. 2 volumes of methanol were added, centrifuged and the samples were analysed by LC/MS/MS using an internal standard: 7(β-hydroxyethyltheophylline), to obtain values of drug concentration in the plasma (ng/mL plasma).

Figure 4:
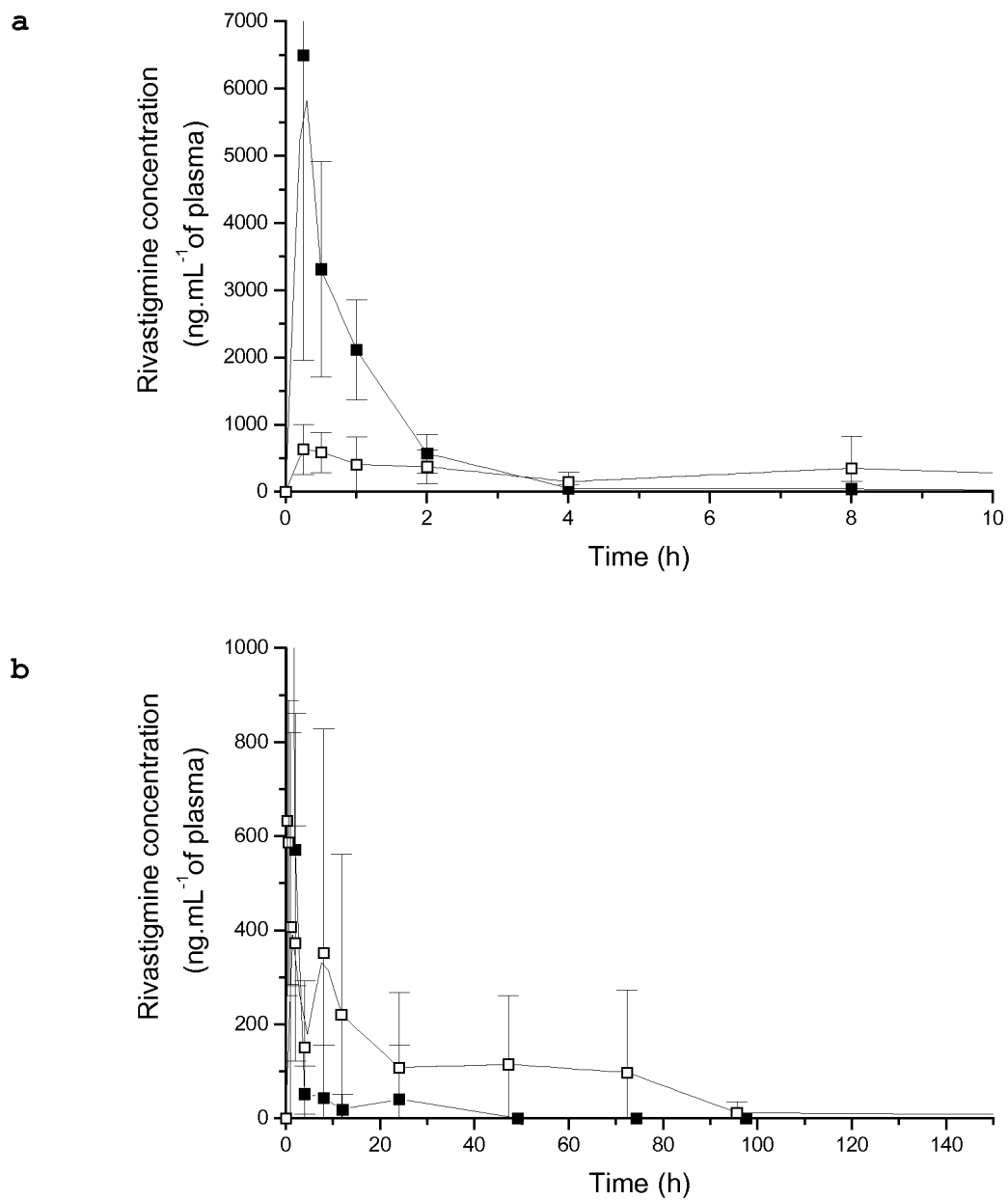
FIG. 4 represents the release of rivastigmine from the organogel after injection into rats. (a) and (b) shows the same data, but the scale of (b) is smaller.

The release of rivastigmine in the animal is sustained during 100 hours (compared to 48 hours without organogelator) and there is no burst of release, highlighting the advantage of using organogels rather than oil formulation. See also FIG. 4.

The invention claimed is:

1. An injectable pharmaceutical composition with gelling properties containing:

an active principle;

a hydrophobic and bio-compatible organic liquid; and an organogelling substance, wherein said organogelling substance is a L-tyrosine derivative of the following formula (I):

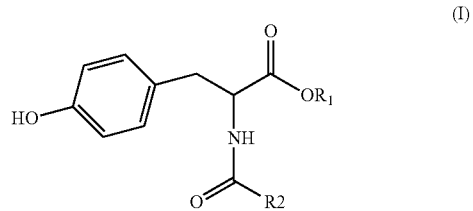

wherein:

R1 is an alkyl group containing 1 to 3 carbon atoms, linear or branched; and

R2 is a hydrophobic group chosen among aliphatic saturated or unsaturated fatty chains or aryl or arylalkyl groups.

2. The composition according to claim 1, wherein R2 is —(CH$_2$)$_n$—CH$_3$ and n is an integer from 10 to 23.

3. The composition according to claim 1, wherein R2 is an unsaturated fatty chain comprising 11 to 24 carbon atoms.

4. The composition according to claim 1, wherein R1 is a methyl or an ethyl group.

5. The composition according to claim 3, wherein the organogelling substance is selected from the group consisting of: N-Behenoyl L-tyrosine methyl ester (B-TyrOCH$_3$), N-Stearoyl L-tyrosine methyl ester (S-TyrOCH$_3$) and N-Lauroyl L-tyrosine methyl ester (L-TyrOCH$_3$).

6. The composition according to claim 1, wherein the organogelling substance is between 0.5% and 10% by weight relative to the total weight of said composition.

7. The composition according to claim 1, wherein the hydrophobic and bio-compatible organic liquid is selected from the group consisting of: vegetable oils, synthetic, semi-synthetic oils, and their mixtures.

8. The composition according to claim 7, wherein the hydrophobic and bio-compatible organic liquid contains mono-, di-, and/or tri-glycerides.

9. The composition according to claim 8, wherein the hydrocarbon chains of said triglycerides are 11 to 24 carbon atoms.

10. The composition according to claim 7, wherein the vegetable oil is selected from the group consisting of: safflower oil, soybean oil, olive oil, corn oil, castor oil, sesame oil, almond oil and their mixtures.

11. The composition according to claim 1, wherein the active principle is dissolved or dispersed into said composition.

12. The composition according to claim 11, wherein the active principle is selected from the group consisting of: drugs, heparin, anticholinesterase, N-methyl-D-aspartate receptor antagonists, proteins, hormones, peptides, amino acids, vitamins, nucleic acids and oligonucleotides.

13. The composition according to claim 1, wherein the active principle is between 0.5 and 5% by weight relative to the total weight of the composition.

14. The composition according to claim 1, further comprising a hydrophilic organic solvent.

15. The composition according to claim 14, wherein said hydrophilic organic solvent is selected from the group consisting of: ethanol, glycerol, benzyl alcohol, propylene glycol, N-methylpyrrolidone and dimethyl sulphoxide, poly (ethylene)glycol of low molecular weight, chlorobutanol, furfural, N,N-dimethyl-acetamide, glycerol formal, isopropylidene-glycerol, ethyl lactate, acetic acid and lactic acid.

16. The composition according to claim 14, wherein the amount of said hydrophilic solvent in the composition is less than 60% by weight of the composition.

17. A medicament comprising the composition according to claim 1.

18. A sustained release composition of active principles into the body comprising the composition according to claim 1.

19. Process for preparing the composition according to claim 1, comprising the three following steps:
   (a) Mixing the active principle, the organogelling substance and the hydrophobic organic liquid all together,
   (b) Heating the mixture obtained in step (a) at a temperature higher than the transition temperature from the gel state to the liquid state of said composition, until complete dissolution of the organogelling substance,
   (c) Cooling the mixture obtained in step (b) at room temperature.

20. Process according to claim 19, wherein a hydrophilic organic solvent is added to the mixture obtained at step (b) before cooling.

21. The composition according to claim 1, wherein R2 is —(CH$_2$)$_n$—CH$_3$ and n is an integer from 16 to 20.

22. The composition according to claim 1, wherein the organogelling substance is between 1% and 5% by weight relative to the total weight of said composition.

23. The composition according to claim 1, wherein the organogelling substance is between 1% and 3% by weight relative to the total weight of said composition.

24. The composition according to claim 8, wherein the hydrocarbon chains of said triglycerides are 17 to 21 carbon atoms.

25. The composition according to claim 11, wherein the active principle is morphine.

26. The composition according to claim 11, wherein the active principle is selected from the group consisting of: rivastigmine, galantamine, and donepezil.

27. The composition according to claim 11, wherein the active principle is memantine.

28. The composition according to claim 11, wherein the active principle is selected from the group consisting of: α or β interferon, antibodies and interleukins.

29. The composition according to claim 11, wherein the active principle is somatostatin or erythropoietin.

30. The composition according to claim 14, wherein the amount of said hydrophilic solvent in the composition is less than 20% by weight of the composition.

31. The composition according to claim 14, wherein the amount of said hydrophilic solvent in the composition is less than 10% by weight of the composition.

* * * * *